(12) United States Patent
Den Boer

(10) Patent No.: US 8,104,347 B2
(45) Date of Patent: Jan. 31, 2012

(54) ULTRASONIC INSPECTION METHOD AND DEVICE FOR PLASTICS WALLS

(75) Inventor: Peter Christian Den Boer, Edmonton (CA)

(73) Assignee: Röntgen Technische Dienst B.V., NC Rotterdam (NL)

( * ) Notice: Subject to any disclaimer, the term of this patent is extended or adjusted under 35 U.S.C. 154(b) by 517 days.

(21) Appl. No.: 12/219,150

(22) Filed: Jul. 16, 2008

(65) Prior Publication Data

US 2009/0114021 A1    May 7, 2009

(51) Int. Cl.
*G01N 29/04* (2006.01)

(52) U.S. Cl. ............ 73/596; 73/597; 73/598; 73/602

(58) Field of Classification Search .......... 73/596, 73/598, 600, 602, 622, 623, 624, 627; 310/334, 310/336
See application file for complete search history.

(56) References Cited

U.S. PATENT DOCUMENTS

| | | | | |
|---|---|---|---|---|
| 4,160,385 A * | 7/1979 | Gromlich et al. | | 73/622 |
| 5,369,998 A * | 12/1994 | Sowerby | | 73/861.04 |
| 6,125,704 A * | 10/2000 | Wang | | 73/602 |
| 6,450,392 B1 * | 9/2002 | Nakamura et al. | | 228/104 |
| 6,476,624 B1 * | 11/2002 | Chuman et al. | | 324/718 |
| 7,089,795 B2 * | 8/2006 | Bray et al. | | 73/598 |
| 7,188,526 B2 * | 3/2007 | Taylor et al. | | 73/618 |
| 7,255,007 B2 * | 8/2007 | Messer et al. | | 73/622 |
| 7,552,631 B2 * | 6/2009 | Harthorn et al. | | 73/152.57 |
| 2003/0226402 A1 | 12/2003 | Leybovich | | |
| 2005/0262927 A1 | 12/2005 | Scott | | |
| 2007/0000329 A1 | 1/2007 | Taylor | | |

FOREIGN PATENT DOCUMENTS

WO  2004/029564  4/2004

OTHER PUBLICATIONS

I.J. Munns et al. "Ultrasonic and Radiographic NDT of Butt Fusion Welds in Polyethylene Pipe," NDTnet Apr. 1996 vol. 1 No. 04.
Munns et al. "Ultrasonic and radiographic NDT of butt fusion welds in polyethylene pipe." vol. 1, No. 4, Apr. 1, 1996.

* cited by examiner

*Primary Examiner* — Jacques M Saint Surin
(74) *Attorney, Agent, or Firm* — Jacobson Holman PLLC

(57) ABSTRACT

A method and system for ultrasonic time of flight diffraction inspection of a plastics wall, such as a pipe wall. The method includes providing an ultrasound transmitter and transmitting an ultrasound signal having a nominal frequency into the wall, providing an ultrasound receiver and receiving the ultrasound signal transmitted through the wall. The ultrasound signal provided by the transmitter has a bandwidth of more than 80%, preferably more than 100% of the nominal frequency of the ultrasound signal provided by the transmitter.

25 Claims, 2 Drawing Sheets

ULTRASONIC INSPECTION METHOD AND DEVICE FOR PLASTICS WALLS

The invention relates to a method for ultrasonic time of flight diffraction testing of plastics walls, more specifically butt fusion welds in plastics pipe systems such as polyethylene pipe systems.

The invention also relates to a system for ultrasonic time of flight diffraction inspection of a plastics wall.

BACKGROUND OF THE INVENTION

The use of polyethylene piping in gas, water and chemical industries can be attributed to its lightness, flexibility and good corrosion resistance, as well as the ease with which the polyethylene pipes can be joined. Joining is commonly performed using the butt fusion or butt welding method. The quality of butt fusion joints in polyethylene pipe systems depends primarily on control of process parameters during welding. Inspection methods are evidently required if one wants to objectively assess butt fusion joint quality.

At one stage a guideline standard (ASTM F600-78) for the manual ultrasonic inspection of butt fusion welds in polyethylene pipe was introduced, which standard was withdrawn again in 1991 for being too dependent on the skill of the operator.

In "Ultrasonic and Radiographic NDT of Butt Fusion Welds in Polyethylene Pipe", NDTnet—April 1996, Vol. 1 No. 04, by I. J. Munns and G. A. Georgiou an ultrasonic Time of Fight Diffraction (ToFD) technique was presented for non-destructively inspecting butt fusion welds in polyethylene pipe systems.

SUMMARY OF THE INVENTION

It is an object of the invention to provide an improved ultrasonic inspection method for inspection of plastics walls, e.g. of pipe systems, more particularly polyethylene pipe systems. The method is arranged for determining the presence and/or absence of a defect in the plastics wall, such as a defect in a butt fusion weld of a plastics pipe system, such as a, preferably high density, polyethylene pipe system.

According to the invention is provided a method for ultrasonic time of flight diffraction inspection of a plastics wall, such as a pipe wall, comprising providing an ultrasound transmitter and transmitting an ultrasound signal into the wall, providing an ultrasound receiver and receiving the ultrasound signal transmitted through the wall, wherein the ultrasound signal provided by the transmitter has a bandwidth of more than approximately 80%, preferably more than 100%, of a nominal frequency of the ultrasound signal provided by the transmitter Preferably, also the receiver has a bandwidth of more than 80%, preferably more than 100%, of the nominal frequency.

Herein, the bandwidth is defined as the bandwidth at −6 dB with respect to the peak frequency (also termed nominal frequency herein) of the ultrasound signal.

When inspecting a plastics wall using ultrasonic time of flight diffraction inspection, the plastics material tends to absorb part of the ultrasound signal provided by the transmitter. The inventor has realised that this absorption in practice may especially affect higher frequencies within the ultrasound signal provided by the transmitter. The plastics wall material may be interpreted as acting as a low pass filter on the ultrasound signal propagating towards the receiver.

Providing the ultrasound signal with the large bandwidth of more than approximately 80% of the nominal frequency of the ultrasound signal provides the advantage that, despite the low pass filtering of the plastics material, the ultrasound signal may contain enough energy to be detected at the receiver. It is for instance possible that the ultrasound transmitter (in free space) provides the ultrasound signal with a nominal frequency of 2.25 MHz and a bandwidth of 100% (i.e. the −6 dB points may be at 1.125 and 3.375 MHz respectively). After transmission through the plastics wall the ultrasound signal detected at the receiver may for instance have a center frequency of 1 MHz or less due to attenuation of mainly the higher frequency components. It will be appreciated that the receiver having the bandwidth of more than 80%, preferably more than 100%, may still be sensitive to the ultrasound signal with the reduced center frequency.

According to an aspect of the invention, the nominal frequency of the ultrasound signal is chosen in dependence of a thickness of the wall. Preferably, the nominal frequency is between about 1 MHz and 4 MHz, preferably about 2.25 MHz, for walls having a thickness of more than approximately 15 mm, between about 3 MHz and 8 MHz, preferably about 5 MHz, for walls having a thickness of less than approximately 15 mm and more than approximately 10 mm, and between about 7 MHz and 25 MHz, preferably about 15 MHz, for walls having a thickness of less than approximately 10 mm. This provides the advantage that the nominal frequency is properly matched to attenuation conditions of the plastics wall.

According to another aspect of the invention, the presence and/or absence of a defect in the wall is determined on the basis of arrival times at the receiver of the ultrasound signal emitted by the transmitter and on the basis of an attenuation of the ultrasound signal emitted by the transmitter when received by the receiver. This provides the advantage that the ToFD method is supplemented with attenuation data, providing a more reliable determination of the presence and/or absence of a defect in the plastics material.

In an embodiment, the wall is a pipe wall of plastics pipe system, such as a polyethylene pipe system.

According to a further aspect of the invention, the method comprises inspecting a first depth region of the wall using the transmitter and receiver, inspecting an other, second, depth region of the wall using ultrasonic time of flight diffraction by providing a further ultrasound transmitter and transmitting a further low frequency ultrasound signal into the wall, providing a further ultrasound receiver and receiving the further ultrasound signal transmitted through the wall. Thus, thick wall may be inspected by (imaginary) dividing the wall into the first and second depth region and inspecting the first depth region using the first transmitter and receiver and inspecting the second depth region using the further, second, transmitter and receiver.

Preferably, an angle of incidence of the ultrasound signal into the wall is different for the transmitter and the further transmitter. Preferably, a field of view of the transmitter and receiver partially overlaps with a field of view of the further transmitter and the further receiver.

According to the invention is also provided a system for ultrasonic time of flight diffraction inspection of a plastics wall, such as a pipe wall, comprising an ultrasound transmitter for transmitting an ultrasound signal having a nominal frequency into the wall, an ultrasound receiver for receiving the ultrasound signal when transmitted through the wall, and a processing unit for determining the presence and/or absence of a defect in the wall on the basis of an arrival time at the receiver of the ultrasound signal emitted by the transmitter, wherein the transmitter is arranged for transmitting the ultrasound signal having a bandwidth of more than 80%, preferably more than 100% of the nominal frequency of the ultrasound signal.

Preferably, the transmitter and receiver have substantially the same nominal frequency and substantially the same bandwidth. In that case operation of the system is independent of specific attenuation of higher frequency components of the ultrasound signal, e.g. independent of a specific wall thickness.

According to the invention is also provided an ultrasound transmitter for ultrasonic inspection of a plastics wall, such as a pipe wall, e.g. a transmitter of the system, wherein the transmitter is arranged for transmitting the ultrasound signal having a bandwidth of more than 80%, preferably more than 100% of the nominal frequency of the ultrasound signal.

Preferably, the transmitter comprises a wedge for abutting the transmitter against a surface of the plastics wall. A speed of sound in the wedge may be lower than a speed of sound in the plastics wall to be inspected. The wedge may e.g. be made of a material having a speed of sound lower than the speed of sound in the plastics wall material. This provides the advantage that the ultrasound may form a beam having a larger angle of incidence with respect to the normal direction in the wall than in the wedge.

Preferably, the wedge has an acoustic impedance substantially equal to an acoustic impedance of the plastics wall to be inspected. The wedge may e.g. be made of a material having an acoustic impedance substantially equal to the acoustic impedance of the plastics wall material, e.g. within ±30%. This provides the advantage that little ultrasound energy is reflected at the interface between the wedge and the plastics wall.

Preferably, the wedge has a low absorption for the ultrasound signal. The wedge may e.g. be made of a material having a low absorption coefficient for the ultrasound signal. This provides the advantage that the influence of the wedge on the inspection may be minimized.

According to the invention also an ultrasound receiver is provided, arranged for receiving the ultrasound signal having a bandwidth of more than 80%, preferably more than 100% of the nominal frequency of the ultrasound signal. The receiver may comprise a wedge similar or identical to the wedge of the transmitter according to the invention.

BRIEF DESCRIPTION OF THE DRAWINGS

The invention will be described by, non-limiting, examples in reference to the accompanying drawing, wherein.

DETAILED DESCRIPTION

Figure 1:
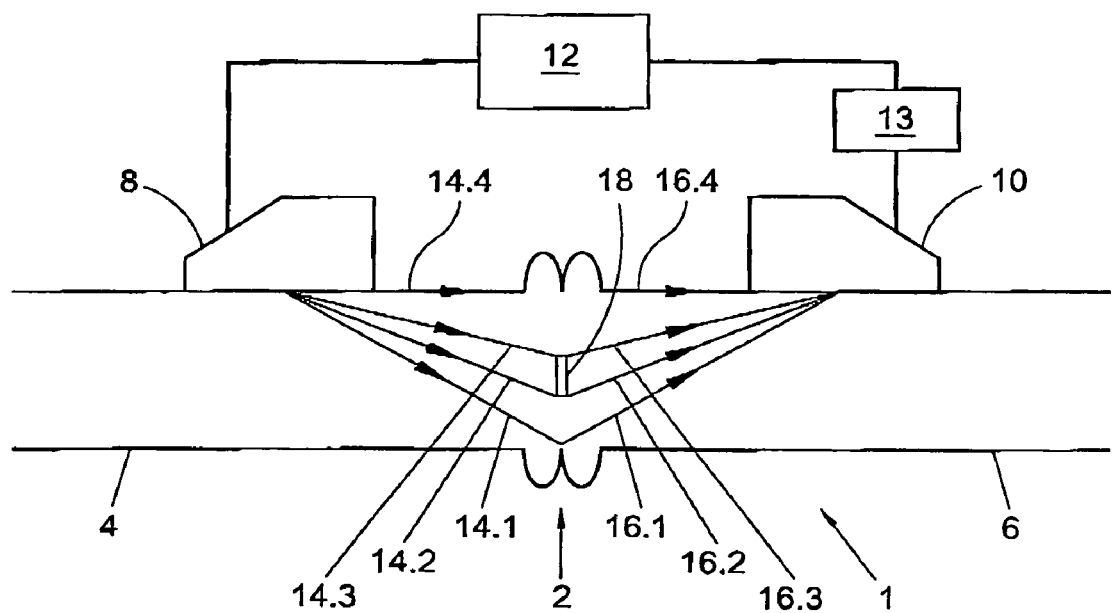
FIG. 1 shows a schematic representation of a first embodiment of a system for ultrasonic time of flight diffraction inspection of a plastics wall, such as a pipe wall, according to the invention.

FIG. 1 shows an embodiment of a system 1 for ultrasonic Time of Flight Diffraction inspection. In this example the system 1 is applied to a butt fusion weld 2 joining two sections 4,6 of high-density polyethylene (HDPE) pipe of PE3408. In this example, the pipe wall 4,6 has a thickness of approximately 22 mm. In this example, the system 1 comprises a transmitter 8 arranged for transmitting low frequency ultrasound into the pipe 4. In this example the nominal frequency of the transmitter is 2.25 MHz. A bandwidth of the transmitter is in this example 2 MHz. More in general, the bandwidth is preferably more than 80%, more preferably more than 100% of the nominal frequency of the transmitter. Herein, the bandwidth is defined as the bandwidth at −6 dB with respect to the nominal frequency of the ultrasound signal.

In this example, the system 1 further comprises a receiver 10 arranged from receiving an ultrasound signal transmitted through the pipe 6. In general the receiver 10 can have a nominal frequency substantially equal to the nominal frequency of the transmitter 8. Also, the bandwidth of the receiver 10 can be substantially equal to the bandwidth of the transmitter 8.

In the example of FIG. 1, the system further comprises a processing unit 12. The processing unit 12 is in this example arranged for controlling the transmitter 8. The processing unit may e.g. comprise a signal generator for generating a high frequency electrical to be converted into the ultrasound signal to be transmitted by the transmitter 8. The processing unit 12 may also be arranged to provide an activation signal to the transmitter for switching the transmitter 8 on or off. The processing unit 12 is in this example further arranged for receiving a(n electrical) signal representative of the ultrasound signal received by the receiver 10. In this example, the system 1 further comprises a pre-amp 13. The pre-amp receives the signal outputted by the receiver 10, amplifies this signal and transmits the amplified signal to the processing unit 12.

The system 1 as described above may be used in a method for ultrasonic Time of Flight Diffraction inspection of a plastics wall as follows.

The processing unit 12 causes the transmitter 8 to transmit the ultrasound signal. Thereto the transmitter 8 is brought into contact with the wall of the first pipe section 4. The ultrasound signal will propagate through the first pipe section wall, as indicated with arrows 14.$i$ ($i$=1,2,3, . . . ) in FIG. 1. Part of the ultrasound signal will propagate through the first pipe section 4 and be incident upon the back wall of the pipe 4, as indicated with arrow 14.1. There, the signal will be reflected and propagate through the second pipe section 6 towards the receiver 10, as indicated with arrow 16.1. This signal is also referred to as "backwall signal". An other part of the ultrasound signal is a compression wave running just below the surface running directly towards the receiver 10, as indicated with arrows 14.4 and 16.4. This signal is also referred to as "lateral wave signal".

A spacing between the transmitter 8 and the receiver 10 is chosen such that the (imagined) beams of the ultrasound transmitted and received, respectively, intersect with an included angle of approximately 120° at 0.8 to 1 times the depth range of interest, covering the depth region where defects are anticipated. The beams may, hence intersect at approximately 0.7 times the wall thickness.

It will be appreciated that the length of a path travelled by the ultrasound signal from the transmitter 8 to the receiver 10 is shorter for the lateral wave signal than for the backwall signal. Hence, a time required for the ultrasound signal to travel from the transmitter 8 to the receiver 10 (time of flight) is shorter for the lateral wave signal than for the backwall signal.

In the example of FIG. 1, the butt fusion weld 2 comprises a defect 18. FIG. 1 also shows a first ray path 14.3, 16.3 travelled by an ultrasound signal reflected from an upper extreme of the defect 18 and a second ray path 14.2, 16.2 travelled by an ultrasound signal reflected from a lower extreme of the defect 18. It will be appreciated that the time required for the ultrasound signal to travel along the first ray path and the second ray path (time of flight) provides information about the position (depth) and size of the defect 18.

The ultrasound signal received by the receiver 10 will contain information relating to the lateral wave signal, the backwall signal and the first and second ray path. In general, the signal received by the receiver will contain information representative of a presence and/or absence of the defect 18. If the defect 18 is present, the signal received at the receiver 10 will contain information representative of the position (depth) and size of the defect. If no defect is present, the signal received at the receiver will substantially only contain the lateral wave signal and the backwall signal.

In this example, the receiver 10 converts the received ultrasound signal into an electronic signal and transmits the electronic signal representative of the received ultrasound signal to the pre-amp 13, which amplifies the signal and transmits this signal to the processing unit 12. In this example, the receiver 10 or the processing unit 12 digitizes the electronic signal representative of the ultrasound signal with a sampling rate of at least four times the nominal receiver frequency. The processing unit 12 may display the received signal, for instance as a D-scan. The D-scan may e.g. comprise 25 A-scans per inch. The presence and/or absence, and optionally the position and/or size of the defect is determined based on the time of flight of the ultrasound signal. If desired, the system 1 may further comprise a scan frame for automatically scanning the transmitter 8 and receiver 10 along the perimeter of the pipe wall for automatically inspecting the entire butt fusion weld for defects.

A calibration of the system 1 may be performed by determining the position and/or size of a known defect in a calibration wall and comparing the determined position and/or size with the known position and/or size. Thus a depth reading of the system 1 may be calibrated.

When inspecting the HDPE pipe wall 4,6, using the system 1, the HDPE material tends to absorb part of the ultrasound signal provided by the transmitter 8. This absorption mainly affects higher frequencies within the ultrasound signal provided by the transmitter 8. The HDPE pipe wall material may be interpreted as acting as a low pass filter on the ultrasound signal propagating through the HDPE pipe wall 4,6.

Having the transmitter 8 provide the ultrasound signal with the large bandwidth of more than approximately 80% of the nominal frequency of the ultrasound signal provides the advantage that, despite the low pass filtering of the HDPE material, the ultrasound signal may still contain enough energy to be detected at the receiver.

In this example the ultrasound transmitter in free space provides the ultrasound signal with a nominal frequency of 2.25 MHz and having the −6 dB points are at 1.25 and 3.25 MHz respectively, i.e. having the bandwidth of approximately 90%. After transmission through the HDPE pipe wall 4,6 the ultrasound signal detected at the receiver 10 in this example has a center frequency of 1.4 MHz and −6 dB points at 1.1 and 1.7 MHz respectively. Thus, the bandwidth has decreased to approximately 40% due to attenuation of mainly the higher frequency components.

It will be appreciated that the thicker the plastics wall is, the more the higher frequency components of the ultrasound signal will be attenuated. Thus, the nominal frequency of the ultrasound signal provided by the transmitter 8 may be chosen in dependence of the thickness of the plastics wall to be inspected. Preferably, the thicker the wall, the lower the nominal frequency.

Thus, while the ultrasound signal travels through the first and/or second pipe section 4,6, the ultrasound signal, especially the higher frequency components thereof, is attenuated.

Figure 2:
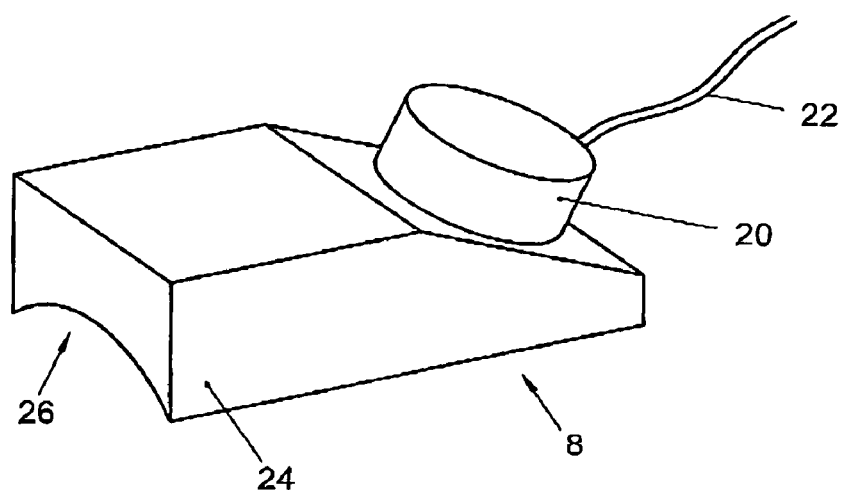
FIG. 2 shows an embodiment of a transmitter of the system according to the invention.

In an advanced embodiment, the processing unit 12 is arranged for determining the presence and/or absence of a defect, and optionally the position and/or size, also on the basis of the attenuation of the ultrasonic signal emitted by the transmitter when received by the receiver and passed on to the pre-amp 13. It will be appreciated that the attenuation, just like the time of flight can be calibrated, and thus may allow more accurate determination of the presence and/or absence, and optionally the position and/or size of the defect. It is for instance possible to correct a position of the defect determined on the basis of the time of flight using a measured attenuation for the ray path corresponding to the defect position. Additionally, or alternatively, the processing unit 12 may be arranged for determining the presence and/or absence of a defect, and optionally the position and/or size, also on the basis of a shift of the center frequency of the ultrasonic signal received by the receiver. It will be appreciated that the frequency shift, just like the time of flight can be calibrated, and thus may allow more accurate determination of the presence and/or absence, and optionally the position and/or size of the defect. It is for instance possible to correct a position of the defect determined on the basis of the time of flight using a measured frequency shift for the ray path corresponding to the defect position. FIG. 2 shows an embodiment of a transmitter 8 of the system 1. The transmitter comprises a transducer 20 arranged for generating the ultrasound signal in response to an electronic signal supplied to the transducer 20 via a wire 22. In this example the transducer 20 comprises a single crystal compression (longitudinal) wave probe. The transmitter 8 further comprises a wedge 24. The wedge 24 is arranged for coupling the ultrasound signal into the pipe wall at a desired angle of incidence relative to the normal to the pipe wall. The desired angle of incidence, within the pipe wall, is preferably between 55° and 70°, for instance approximately 60°.

Preferably the wedge material has a speed of sound c lower than the speed of sound of the plastics wall material, in this example lower than the speed of sound in the HDPE material. Thus, when refracting at an interface between the wedge and the pipe wall, the beam of ultrasound has a larger angle of incidence in the wall material than in the wedge material.

In this example, the wedge is made of polymethylpentene. Polymethylpentene (TPX) has a speed of sound of approximately 2030 m/sec which is lower than the speed of sound in HDPE (approximately 2431 m/sec). It is noted that polymethylmethacrylate (Perspex), which is a common wedge material, has a speed of sound of approximately 2730 m/sec, which is higher than the speed of sound in HDPE and thus not preferred.

The acoustic impedance Z of a material is defined as the product of the density $\rho$ (rho) (kg/m$^3$) and speed of sound c (m/s) of that material. Z is expressed in kg/m$^2$ s. Preferably the acoustic impedance Z of the wedge material is close to the acoustic impedance of the plastics wall material. Thus, reflection of ultrasound signal at the interface between the wedge and the wall is minimized, so sensitivity is maximized. Preferably, the acoustic impedance is between 0.7 and 1.3 times the acoustic impedance of the wall material, more preferably between 0.85 and 1.15 times.

For HDPE $\rho$ is approximately 960 kg/m$^3$, c is approximately 2431 m/s, and hence Z is approximately 2,3.106 kg/m$^2$ s. For polymethylpentene $\rho$ is approximately 830 kg/m$^3$, c is approximately 2030 m/s, and hence Z is approximately 1,8.106 kg/m$^2$ s. For polymethylmethacrylate $\rho$ is approximately 1190 kg/m$^3$, c is approximately 2730 m/s, and hence Z is approximately 3,2.106 kg/m² s. Hence, also with respect to acoustic impedance polymethylpentene is a suitable wedge material.

Preferably, the wedge has a low absorption for the ultrasound signal. The wedge may e.g. be made of a material having a low absorption coefficient.

In the example of FIG. 2 the wedge 24 has a concave lower face 26. A radius of curvature of the concave lower face matches a radius of curvature of the outside face of the pipe wall 4. Thus, the wedge 24 makes good contact with the pipe wall so that ultrasound can be transmitted from the wedge 24 into the wall 4 efficiently. If desired a couplant, such as a water-based couplant can be inserted between the wedge 24 and the pipe 4.

It will be appreciated that the receiver 10 of the system may be provided with a transducer for receiving the ultrasound signal and a wedge similar to the wedge of the transmitter as described with respect to FIG. 2.

It has been found that the nominal transmitter frequency should preferably be chosen in dependence of the wall thickness of the pipe 4,6. For relatively thick walls of more than 15 mm, e.g. 22 mm, the low nominal frequency of 1-4 MHz, for instance approximately 2.25 MHz is preferred. For intermediate wall thicknesses of approximately 10-15 mm a nominal frequency of approximately 3-8 MHz, for instance 5 MHz is preferred. For relatively thin walls of less than 10 mm, a nominal frequency of 7-25 MHz, for instance 15 MHz is preferred. These preferred nominal frequencies provide the advantage that the ultrasound signal is not attenuated too much within the wall while providing good spatial resolution for detecting the presence and/or absence, and optionally the position and/or size, of the defect.

In an embodiment, the transducer 20 for generating the ultrasound signal is a single crystal probe. Preferably, a size of the crystal is inversely proportional to the nominal frequency of the transmitter/receiver. The transmitter transmitting at 2.25 MHz may for instance have a crystal with a cross sectional diameter of approximately 12.7 mm (0.5"). The transmitter transmitting at 15 MHz may for instance have a crystal with a cross sectional diameter of approximately 3.2 mm (0.125") to approximately 6.4 mm (0.25").

Figure 3:
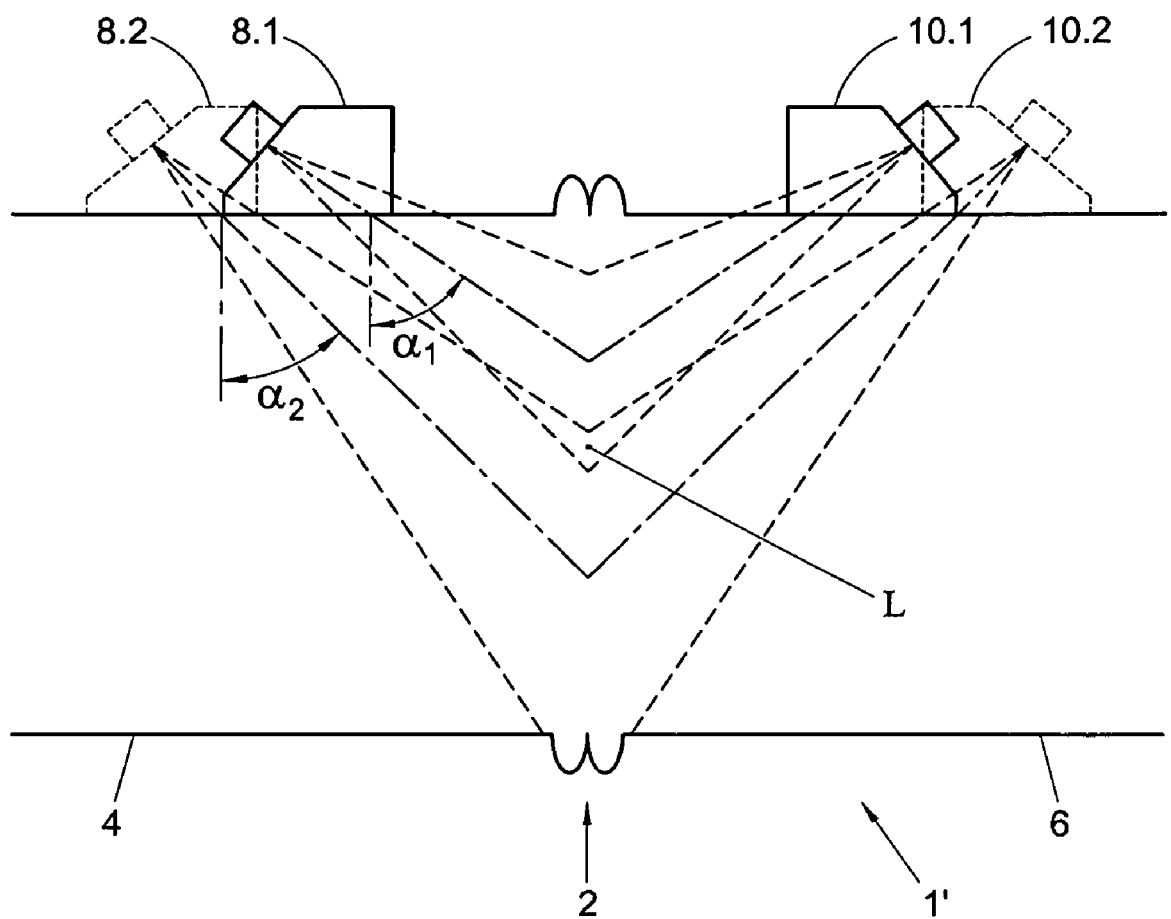
FIG. 3 shows a schematic representation of a system for inspecting a thick plastics wall according to the invention.

For very thick wall thicknesses of e.g. more than 70-80 mm, the wall may be scanned for defects in two zones. FIG. 3 shows an example of a system 1' for ultrasonic ToFD inspection of such very thick wall 4,6. The system 1' comprises a first set of a first transmitter 8.1 and a first receiver 10.1 for providing and detecting the ultrasound signal at a first angle of incidence $\alpha_1$. The system 1' further comprises a second set of a second transmitter 8.2 and a second receiver 10.2 for providing and detecting the ultrasound signal at a second angle of incidence $\alpha_2$. The first angle of incidence $\alpha_1$ is in this example approximately 60°, while the second angle of incidence $\alpha_2$ is approximately 45°. For the very thick wall thickness the very low nominal frequency is preferred. The first set of the transmitter 8.1 and the receiver 10.1 will then detect the lateral wave signal. The second set of the transmitter 8.2 and the receiver 10.2 will then detect the backwall signal. In FIG. 3 it can be seen that the detection areas of the first set and the second set overlap at L. Thus, the two sets combined allow to inspect the entire thickness, at least the entire area of interest, of the very thick wall. It will be appreciated that the first set and the second set need not be applied to the wall simultaneously.

Table 1 provides examples of the angle of incidence (Probe angle), nominal transmitter and receiver frequency (Probe Frequency) and separation between the transmitter and the receiver (Probe separation (index to weld center line)). In the examples of table 1 the separation is indicated as the sum of the effective distance of the transmitter to the weld center line and the effective distance of the receiver to the weld center line.

TABLE 1

| Pipe Wall Thickness (mm) | Probe angle (deg) | Probe Frequency (MHz) | Probe separation (index to WCL in mm.) |
|---|---|---|---|
| 6.0-7.2 | 60° | 15.0 | 15 + 15 |
| 11.0-13.7 | 60° | 5.0 | 22 + 22 |
| 22.0 | 60° | 2.25 | 34 + 34 |
| 38.1-50.8 | 60° | 2.25 | 60 + 60 |
| 110 | 45° | 2.25 | 83 + 83 |
|  | 60° | 2.25 | 53 + 53 |
| 130 | 45° | 2.25 | 93 + 93 |
|  | 60° | 2.25 | 60 + 60 |

In the foregoing specification, the invention has been described with reference to specific examples of embodiments of the invention. It will, however, be evident that various modifications and changes may be made therein without departing from the broader spirit and scope of the invention as set forth in the appended claims.

In the examples polyethylene of the type PE3408 is used. However, other types of polyethylene can be used such as PE4710. Also, other types of plastics may be inspected according to the invention.

In the examples, the wall is a pipe wall. It will be appreciated that the wall may also be e.g. a substantially flat wall.

However, other modifications, variations and alternatives are also possible. The specifications, drawings and examples are, accordingly, to be regarded in an illustrative rather than in a restrictive sense.

In the claims, any reference signs placed between parentheses shall not be construed as limiting the claim. The word 'comprising' does not exclude the presence of other features or steps then those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to advantage.

The invention claimed is:

1. A method for ultrasonic time of flight diffraction inspection of a plastics wall, such as a pipe wall, said method comprising:
   providing an ultrasound transmitter and a wedge for abutting the transmitter against a surface of the plastics wall, a speed of sound in the wedge being lower than a speed of sound in the plastics wall to be inspected, and transmitting an ultrasound signal having a nominal frequency into the wall,
   providing an ultrasound receiver and receiving the ultrasound signal transmitted through the wall,
   the ultrasound signal provided by the transmitter having a bandwidth of more than 80% of the nominal frequency of the ultrasound signal provided by said transmitter.

2. The method according to claim 1, wherein the nominal frequency of the ultrasound signal is chosen in dependence of a wall thickness of the wall.

3. The method according to claim 2, wherein the nominal frequency is
   between about 1 MHz and 4 MHz for walls having a thickness of more than approximately 15 mm, between about 3 MHz and 8 MHz for walls having a thickness of less than approximately 15 mm and more than approximately 10 mm, and between about 7 MHz and 25 MHz for walls having a thickness of less than approximately 10 mm.

4. The method according to claim 1, further comprising at least one of determining the presence and determining absence of a defect in the wall on the basis of arrival times at the receiver of the ultrasound signal emitted by the transmitter and on the basis of an attenuation of the ultrasound signal emitted by the transmitter when received by the receiver.

5. The method according to claim 1, wherein the wall is a polyethylene pipe system.

6. The method according to claim 1, wherein the method further comprising
inspecting a first depth region of the wall using the transmitter and receiver,
inspecting an other, second, depth region of the wall using ultrasonic time of flight diffraction by
providing a further ultrasound transmitter and transmitting a further ultrasound signal into the wall,
providing a further ultrasound receiver and receiving the further ultrasound signal transmitted through the wall.

7. The method according to claim 6, wherein an angle of incidence of the ultrasound signal into the wall is different for the transmitter and the further transmitter.

8. The method according to claim 1, wherein the ultrasound receiver has a bandwidth of more than 80% of the nominal frequency.

9. A system for ultrasonic time of flight diffraction inspection of a plastics wall, such as a pipe wall, comprising:
an ultrasound transmitter for transmitting an ultrasound signal having a nominal frequency into the wall,
a wedge for abutting the transmitter against a surface of the plastics wall, a speed of sound in the wedge being lower than a speed of sound in the plastics wall to be inspected,
an ultrasound receiver for receiving the ultrasound signal when transmitted through the wall, and
a processing unit for determining at least one of the presence and absence of a defect in the wall on the basis of an arrival time at the receiver of the ultrasound signal emitted by the transmitter,
said transmitter being arranged for transmitting the ultrasound signal having a bandwidth of more than 80% of the nominal frequency of the ultrasound signal.

10. The system according to claim 9, wherein the receiver is arranged for receiving the ultrasound signal having a bandwidth of more than 80% of the nominal frequency of the ultrasound signal.

11. The system according to claim 9, wherein the nominal frequency of the ultrasound signal is chosen in dependence of a wall thickness of the wall.

12. The system according to claim 11, wherein the nominal frequency is
between about 1 MHz and 4 MHz for walls having a thickness of more than approximately 15 mm,
between about 3 MHz and 8 MHz for walls having a thickness of less than approximately 15 mm and more than approximately 10 mm, and
between about 7 MHz and 25 MHz for walls having a thickness of less than approximately 10 mm.

13. The system according to claim 9, wherein the processing unit is arranged for determining at least one of the presence and absence of the defect in the wall further on the basis of an attenuation of the ultrasound signal emitted by the transmitter when received by the receiver.

14. The system according to claim 9, wherein the processing unit is further arranged for determining at least one of a position and size of the defect.

15. The system according to claim 9, further comprising
a further ultrasound transmitter for transmitting a further ultrasound signal into the wall, and
a further ultrasound receiver for receiving the further ultrasound signal transmitted through the wall,
the processing unit being arranged for determining at least one of the presence and absence of a defect in a first depth region of the wall on the basis of an arrival time at the receiver of the ultrasound signal emitted by the transmitter and for determining at least one of the presence and absence of a defect in a second depth region of the wall on the basis of an arrival time at the further receiver of the further ultrasound signal emitted by the further transmitter.

16. The system according to claim 15, wherein an angle of incidence of the ultrasound signal into the wall is different for the transmitter and the further transmitter.

17. An ultrasound transmitter for ultrasonic inspection of a plastics wall, such as a pipe wall, said ultrasound transmitter comprising
a transmitter transmitting an ultrasound signal having a bandwidth of more than 80% of the nominal frequency of the ultrasound signal, and
a wedge for abutting the transmitter against a surface of the plastics wall, a speed of sound in the wedge being lower than a speed of sound in the plastics wall to be inspected.

18. The ultrasound transmitter according to claim 17, wherein the wedge has an acoustic impedance substantially equal to an acoustic impedance of the plastics wall to be inspected.

19. The ultrasound transmitter according to claim 17, wherein the wedge has a low absorption for the ultrasound signal.

20. The method according to claim 1, wherein the ultrasound signal has a bandwidth of more than 100% of the nominal frequency of the ultrasound signal.

21. The system according to claim 9, wherein the ultrasound signal has a bandwidth of more than 100% of the nominal frequency of the ultrasound signal.

22. The method according to claim 1, wherein the wedge has an acoustic impedance substantially equal to an acoustic impedance of the plastics wall to be inspected.

23. The method according to claim 1, wherein the wedge has a low absorption for the ultrasound signal.

24. The system according to claim 9, wherein the wedge has an acoustic impedance substantially equal to an acoustic impedance of the plastics wall to be inspected.

25. The system according to claim 9, wherein the wedge has a low absorption for the ultrasound signal.

* * * * *

UNITED STATES PATENT AND TRADEMARK OFFICE
CERTIFICATE OF CORRECTION

PATENT NO.         : 8,104,347 B2
APPLICATION NO.    : 12/219150
DATED              : January 3, 2012
INVENTOR(S)        : Peter Christiaan Den Boer Page 1 of 1

It is certified that error appears in the above-identified patent and that said Letters Patent is hereby corrected as shown below:

On the cover page, line 75: "Inventor: Peter Christian Den Boer, Edmonton (CA)" should be -- Inventor: Peter Christiaan Den Boer, Edmonton (CA) --

Signed and Sealed this
Third Day of April, 2012

David J. Kappos
*Director of the United States Patent and Trademark Office*